United States Patent
Su et al.

(10) Patent No.: US 6,582,938 B1
(45) Date of Patent: Jun. 24, 2003

(54) AMPLIFICATION OF NUCLEIC ACIDS

(75) Inventors: Xing Su, Cupertino, CA (US); Helin Dong, Palo Alto, CA (US); Thomas B. Ryder, Los Gatos, CA (US)

(73) Assignee: Affymetrix, Inc., Santa Clara, CA (US)

( * ) Notice: Subject to any disclaimer, the term of this patent is extended or adjusted under 35 U.S.C. 154(b) by 26 days.

(21) Appl. No.: 09/854,317

(22) Filed: May 11, 2001

(51) Int. Cl.⁷ .................. C12P 19/34; C07H 21/02; C12Q 1/68

(52) U.S. Cl. ............... 435/91.2; 435/6; 435/91.21; 536/22.1; 536/23.1; 536/24.3

(58) Field of Search .................. 435/6, 91.2, 91.21; 536/22.1, 23.1, 24.3

(56) References Cited

U.S. PATENT DOCUMENTS

| | | |
|---|---|---|
| 4,357,421 A | 11/1982 | Emtage et al. |
| 4,683,195 A | 7/1987 | Mullis et al. |
| 4,683,202 A | 7/1987 | Mullis |
| 5,409,818 A | 4/1995 | Davey et al. |
| 5,437,990 A | 8/1995 | Burg et al. |
| 5,480,784 A | 1/1996 | Kacian et al. |
| 5,545,522 A | 8/1996 | Van Gelder et al. |
| 5,554,517 A | 9/1996 | Davey et al. |
| 5,716,785 A | 2/1998 | Van Gelder et al. |
| 5,849,547 A * | 12/1998 | Cleuziat et al. .......... 435/91.21 |
| 5,891,636 A | 4/1999 | Van Gelder et al. |
| 6,027,913 A * | 2/2000 | Sommer .................... 435/69.1 |
| 6,063,603 A | 5/2000 | Davey et al. |
| 6,203,984 B1 | 3/2001 | Hu et al. |
| 6,207,372 B1 | 3/2001 | Shuber |
| 6,207,379 B1 | 3/2001 | Lee et al. |

FOREIGN PATENT DOCUMENTS

| WO | WO 99/43850 | * | 9/1999 |
|---|---|---|---|

OTHER PUBLICATIONS

Kwoh et al., Transcription–based amplification system and detection of amplified human immunodeficiency virus type 1 with a bead–based sandwich hybridization format, Proc. Natl. Acad. Sci. USA, vol. 86, pp. 1173–1177, (1989).

* cited by examiner

*Primary Examiner*—Jeffrey Fredman
(74) *Attorney, Agent, or Firm*—Sandra Wells; Philip L. McGarrigle (57) ABSTRACT

The present invention relates to the amplification of nucleic acids, preferably from mRNA. A primer and promoter are added to a target sequence to be amplified and then the target is amplified in an in vitro transcription reaction.

15 Claims, 2 Drawing Sheets

1st strand cDNA synthesis

5' AAAAAAAAAAAAAAAAAAAAAAAAAAA3' mRNA
3' TTTTTTTTTTTTTTTTTTTTTACTGCCACTTAGGCGGAG5' 1st strand cDNA Final product after 2nd strand cDNA synthesis 5' AAAAAAAAAAAAAAAAAAAAAAAATGACGGTGAATCCGCCTC3' 2nd strand cDNA
3' TTTTTTTTTTTTTTTTTTTTTACTGCCACTTAGGCGGAG5' 1st strand cDNA 3rd strand cDNA w/ the blocked Promoter 5' AAAAAAAAAAAAAAAAAAAAAAAATGACGGTGAATCCGCCTC3'
3' TTTTTTTTTTTTTTTTTTTTTACTGCCACTTAGGCGGAG5'
3' *ACTGCCACTTAGGCGGAGGGATATCACTCAGCATAATGTTAAGTGACCGG5'

Final product after the 3rd strand cDNA synthesis with Klenow

5' AAAAAAAAAAAAAAAAAAAAAAAATGACGGTGAATCCGCCTCCCTATAGTGAGTCGTATTACAATTCACTGGCC3'
3' *ACTGCCACTTAGGCGGAGGGATATCACTCAGCATAATGTTAAGTGACCGG5'

SEQUENCE LISTING

<160> NUMBER OF SEQ ID NOS: 5

<210> SEQ ID NO 1
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 1
aaaaaaaaaa aaaaaaaaaa aaaa                                          24

<210> SEQ ID NO 2
<211> LENGTH: 42
<212> TYPE: DNA
<213> ORGANISM: artificial sequence
<220> FEATURE:
<223> OTHER INFORMATION: synthetic oligonucleotide

<400> SEQUENCE: 2
gaggcggatt caccgtcatt tttttttttt tttttttttt tt                      42

<210> SEQ ID NO 3
<211> LENGTH: 42
<212> TYPE: DNA
<213> ORGANISM: artificial sequence
<220> FEATURE:
<223> OTHER INFORMATION: synthetic oligonucleotide

<400> SEQUENCE: 3
aaaaaaaaaa aaaaaaaaaa aaaatgacgg tgaatccgcc tc                      42

<210> SEQ ID NO 4
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 4
ggccagtgaa ttgtaatacg actcactata gggaggcgga ttcaccgtca              50

<210> SEQ ID NO 5

-continued

```
<211> LENGTH: 71
<212> TYPE: DNA
<213> ORGANISM: artificial sequence
<220> FEATURE:
<223> OTHER INFORMATION: synthetic oligonucleotide

<400> SEQUENCE: 5
aaaaaaaaaa aaaaaaaaaa atgacggtga atccgcctcc ctatagtgag tcgtattaca        60
attcactggc c                                                            71
```

AMPLIFICATION OF NUCLEIC ACIDS

FIELD OF THE INVENTION

The present invention relates generally to the amplification of nucleic acids. More specifically, the present invention facilitates the amplification of mRNA for a variety of end uses.

BACKGROUND OF THE INVENTION

Those skilled in the art know there are many ways to synthesize first strand cDNA from mRNA (see, e.g., Sambrook et al., Molecular Cloning: A Laboratory Manual (2nd ed.), Vols. 1–3, Cold Spring Harbor Laboratory, (1989), or Current Protocols in Molecular Biology, F. Ausubel et al., ed. Greene Publishing and Wiley-Interscience, New York (1987)). For example, the first strand cDNA can be synthesized by a reverse transcriptase with a primer. Reverse transcriptases are readily available from many sources and those skilled in the art will know what reverse transcriptase to use for their specific purposes.

Other suitable amplification methods include the ligase chain reaction (LCR) e.g., Wu and Wallace, *Genomics* 4, 560 (1989) and Landegren et al., *Science* 241, 1077 (1988), Burg, U.S. Pat. Nos. 5,437,990, 5,215,899, 5,466,586, 4,357,421, Gubler et al., 1985, Biochemica et Biophysica Acta, Displacement Synthesis of Globin Complementary DNA: Evidence for Sequence Amplification, transcription amplification, Kwoh et al., *Proc. Natl. Acad. Sci. USA* 86, 1173 (1989), self-sustained sequence replication, Guatelli et al., *Proc. Nat. Acad. Sci. USA*, 87, 1874 (1990) and WO 88/10315 and WO 90/06995 and nucleic acid based sequence amplification (NABSA). The latter two amplification methods include isothermal reactions based on isothermal transcription, which produce both single-stranded RNA (ssRNA) and double-stranded DNA (dsDNA) as the amplification products in a ratio of about 30 or 100 to 1, respectively. Second strand priming can occur by hairpin loop formation, RNAse H digestion products, and the 3' end of any nucleic acid present in a reaction capable of forming an extensible complex with the first strand DNA.

Common amplification procedures can encounter problems when adding transcriptional promoters. When promoters are incorporated early during amplification, partial degradation is often observed as a result of the 5' to 3' exonuclease activity of DNA polymerases. Second, amplification that relies upon promoter sequences being incorporated into the primer allows for only one promoter orientation, sense or antisense. Third, the use of short primers (less than 50 bases) ensures greater product reliability than use of longer primers (greater than 50 bases) such as those that include transcriptional promoters.

SUMMARY OF THE INVENTION

The present invention provides a method for the amplification of nucleic acids that may comprise synthesizing double-stranded DNA from a single-stranded DNA population, and producing multiple copies of RNA from the double-stranded DNA More specifically, the method comprises contacting a mRNA having a poly dA tail with a primer comprising poly d(T) and a second sequence; generating a first cDNA strand from the mRNA strand by extending the primer by reverse transcriptase and the appropriate nucleotides under the appropriate conditions, which creates a RNA:DNA duplex; denaturing the RNA:DNA duplex; forming a double stranded DNA; denaturing the double stranded DNA to form a single stranded DNA and adding a promoter to the single stranded DNA, the promoter comprising a complement to the second sequence and a full or partial RNA promoter sufficient to form a functional promoter when the promoter is hybridized to the single stranded DNA; forming a double stranded DNA promoter region by adding the appropriate reagents; and, producing multiple copies of RNA from the DNA strand comprising the promoter. Preferably, the promoter is blocked from 3' extension.

Among other factors, the present invention provides a new method for amplification of nucleic acids. Additionally, the present method is an amplification method in which a promoter is protected from degradation throughout the method.

The present invention also preferably provides methods, which may further comprise contacting the multiple copies of RNA with a solid support comprising nucleic acid probes, and detecting the presence or absence of hybridization of the RNA to the nucleic acid probes on the solid support. In a preferred embodiment, the solid support, which may comprise nucleic acid probes, can be selected from the group consisting of a nucleic acid probe array, a membrane blot, a microwell, a bead, and a sample tube.

In yet another preferred embodiment, the invention relates to a kit comprising reagents and instructions for the amplification of mRNA. Preferably, the kit includes a reaction vessel containing one or more reagents in concentrated form, where the reagent may be an enzyme or enzyme mixture. The kit also includes a container, instructions for use, a promoter which comprises a poly d(T) sequence operably linked to a second sequence, a promoter comprising the second sequence or its equivalent and a sequence that will complete a promoter when annealed to a target and formed into a double stranded DNA. Preferably, the promoter is blocked from extending in the 3' direction.

DETAILED DESCRIPTION OF THE PREFERRED EMBODIMENTS

General

The present invention relies on many patents, applications and other references for details known to those of the art. Therefore, when a patent, application, or other reference is cited or repeated below, it should be understood that it is incorporated by reference in its entirety for all purposes as well as for the proposition that is recited.

As used in the specification and claims, the singular form "a," "an," and "the" include plural references unless the context clearly dictates otherwise. For example, the term "an agent" includes a plurality of agents, including mixtures thereof. An individual is not limited to a human being but may also be other organisms including but not limited to mammals, plants, bacteria, or cells derived from any of the above.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 ect., as well as individual numbers within that range, for example, 1, 2, 3, 4, 5, and 6. This applies regardless of the breadth of the range.

The practice of the present invention may employ, unless otherwise indicated, conventional techniques of organic chemistry, polymer technology, molecular biology (including recombinant techniques), cell biology, biochemistry, and immunology, which are within the skill of the art. Such conventional techniques include polymer array synthesis, hybridization, ligation, detection of hybridization using a label. Specific illustrations of suitable techniques can be had by reference to the example hereinbelow. However, other equivalent conventional procedures can, of course, also be used. Such conventional techniques can be found in standard laboratory manuals such as *Genome Analysis: A Laboratory Manual Series* (*Vols. I–IV*), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), all of which are herein incorporated in their entirety by reference for all purposes.

Methods and techniques applicable to array synthesis have been described in U.S. Pat. Nos. 5,143,854, 5,242,974, 5,252,743, 5,324,633, 5,384,261, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, and 6,090,555, which are all incorporated herein by reference in their entirety for all purposes.

Additionally, gene expression monitoring and sample preparation methods can be shown in U.S. Pat. Nos. 5,800, 992, 6,040,138, and 6,013,449.

Definitions

Nucleic acids according to the present invention may include any polymer or oligomer of pyrimidine and purine bases, preferably cytosine, thymine, and uracil, and adenine and guanine, respectively. See Albert L. Lehninger, Principles of Biochemistry, at 793–800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states. Oligonucleotide and polynucleotide are included in this definition and relate to two or more nucleic acids in a polynucleotide. See U.S. Pat. No. 6,156,501 which is hereby incorporated by reference in its entirety.

Array

An array comprises a support, preferably solid, with nucleic acid probes attached to said support. Arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744, 305, 5,677,195, 6,040,193, 5,424,186 and Fodor et al., Science, 251:767–777 (1991). Each of which is incorporated by reference in its entirety for all purposes. These arrays may generally be produced using mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as fiber optics, glass or any other appropriate substrate. (See U.S. Pat. Nos. 5,770,358, 5,789,162, 5,708,153, 6,040,193 and 5,800,992, which are hereby incorporated by reference in their entirety for all purposes.)

Arrays may be packaged in such a manner as to allow for diagnostics or can be an all-inclusive device; e.g., U.S. Pat. Nos. 5,856,174 and 5,922,591 incorporated in their entirety by reference for all purposes. (See also U.S. patent application Ser. No. 09/545,207 for additional information concerning arrays, their manufacture, and their characteristics.) It is hereby incorporated by reference in its entirety for all purposes.

Preferred arrays are commercially available from Affymetrix under the brand name GeneChip® and are directed to a variety of purposes, including gene expression monitoring for a variety of eukaryotic and prokaryotic species. See Affymetrix Inc., Santa Clara and their website at affymetrix.com.

The Process

In general, the presently preferred invention enables a user to amplify mRNA (a target sequence) for gene expression monitoring experiments. Although one of skill in the art will recognize that other uses may be made of the amplified nucleic acid. An overview of the process is as follows (see FIG. 1). mRNA is contacted with a poly d(T) primer preferably having a unique sequence attached to the poly d(T) (hereinafter the "Primer"). The unique sequence can be one that has no function and can operate as a 'tag' or 'adapter', but it must be one that will not cross hybridize to other nucleic acids that can be present. It may be a repeated section of one or more of the individual bases, such as poly d(T), or a combination of several. Also, the unique sequence can contain a partial promoter sequence (for the later in vitro transcription [IVT] reaction), or a combination of both.

Figure 1:
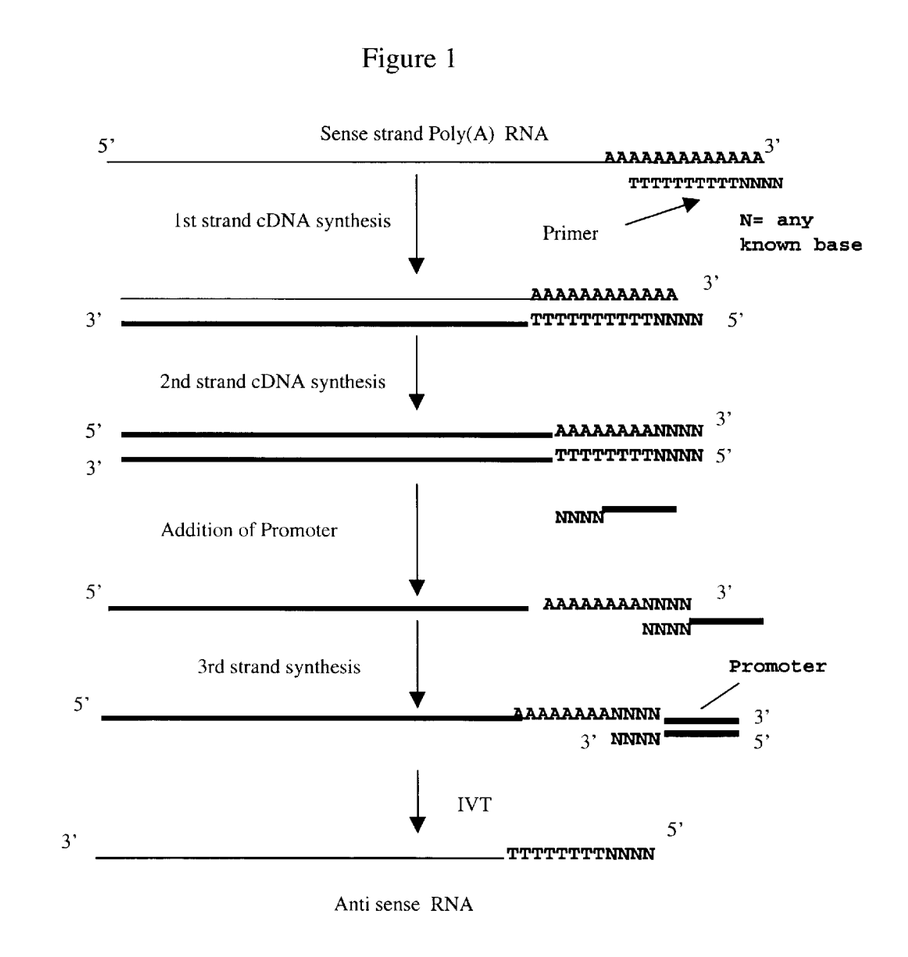
FIG. 1 depicts an overview of a preferred embodiment of the amplification methods of the present invention.

The first DNA strand is synthesized, the mRNA strand can be denatured (but, it is not necessary), and then a second DNA strand is synthesized using conventional methods. A DNA strand is added (hereinafter called the "Promoter"), which contains the unique sequence that was added on with the poly d(T) and a functional promoter or the remainder of the promoter if the unique sequence contained a portion of the promoter already. The portion of the Promoter that is single stranded is filled in (made double stranded) so that there is a functional promoter operably linked to the target sequence. Thereafter, the appropriate reagents are added to transcribe the target portion in an IVT reaction. Preferably, the Promoter is constructed so that it does not serve as a primer for extension of a sequence that is complementary to the target sequence, i.e. it is blocked. Blocking the end of a nucleic acid is known to one of skill in the art.

Also, in one alternative embodiment, the Primer can contain a poly d(T) or one in which T may be partially replaced by U in the Primer. After 2nd cDNA synthesis, the U can be digested by uridine glycosidase, which allows efficient annealing of the Promoter to the cDNA.

Figure 2:
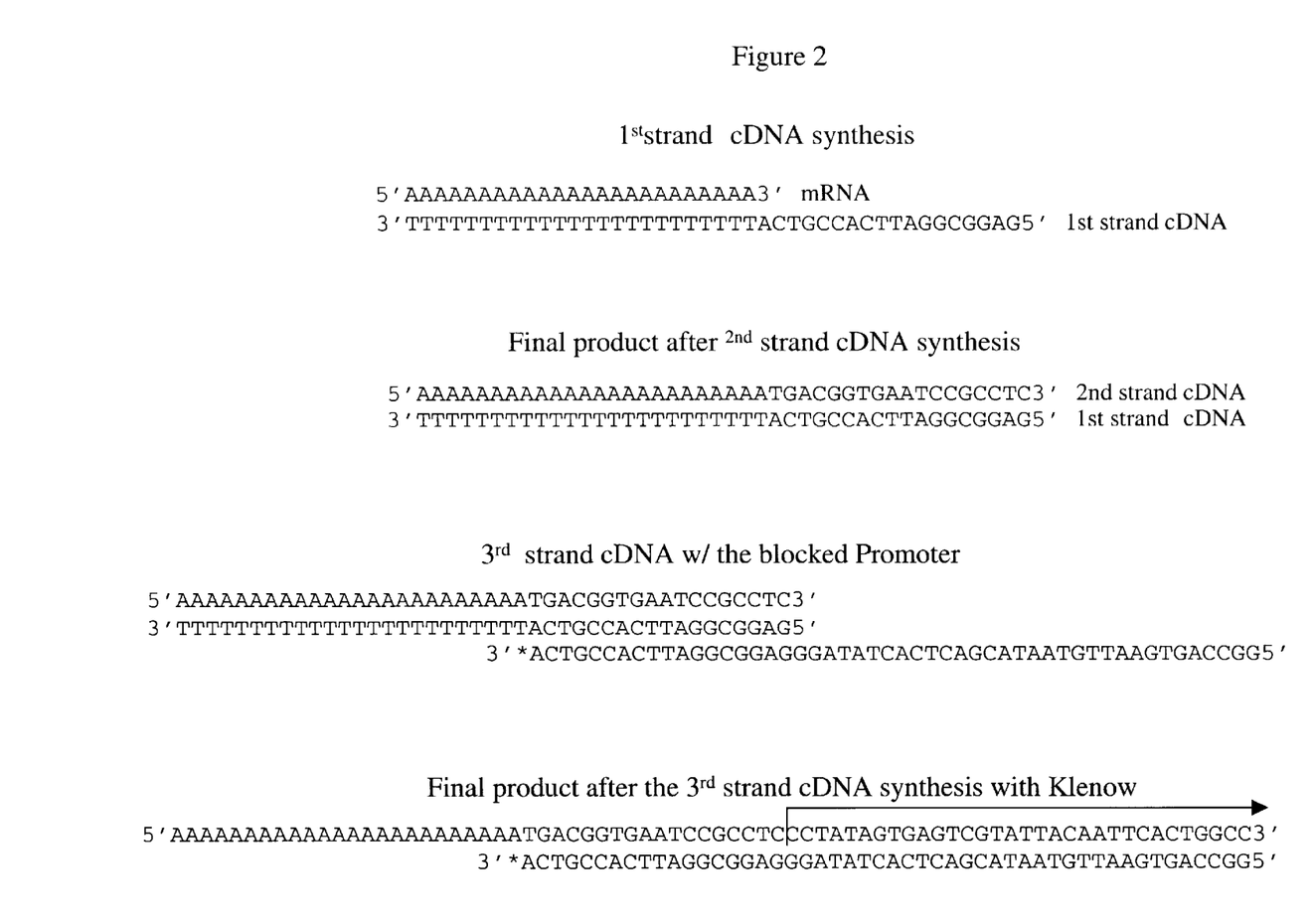
FIG. 2 depicts an aspect of a preferred embodiment of the invention in which a primer (SEQ ID NO: 2) is used to create a DNA strand (SEQ ID NO: 3) and in a subsequent step a blocked oligonucleotide (SEQ ID NO: 4) is used as a template to extend a poly A DNA strand with Klenow DNA polymerase to build a functional T7 promoter (SEQ ID NO: 5). Subsequently, T7 RNA polymerase will use the sense strand as a template to make cRNA resulting in antisense labeled cRNA.

A graphical representation of this system using a unique sequence in the Primer and the functional T7 promoter in the Promoter is shown in FIG. 2. The primer is
5' GAGGCGGATTCACCGT-CATTTTTTTTTTTTTTTTTTTTTTT 3' (SEQ ID NO: 2) and the Promoter is
5' GGCCAGTG AATTGTAATACGACTCACTATAGGGAGGCG GATTCACCGTCA*3' (SEQ ID NO: 4), where the "*" can be a phosphate or an amino group or a dideoxy base, for example. The blocked oligo is used as a template to extend the poly A strand to build a functional T7 promoter. T7 RNA polymerase will use the sense strand as a template to make cRNA resulting in antisense labeled cRNA. The functional T7 promoter sequence is underlined.

5' GGCCAGTG
AATTGTAATACGACTCACTATAGGGAGGCGG-(T)24 3'

More specifically, the presently preferred invention is as follows: PolyA+ containing mRNA or total RNA is annealed with the single-stranded oligo d(T)-tailed primer, such as $T_{20}$ or $T_xN_x$, creating a Primer-template mixture. First strand cDNA synthesis is accomplished by combining the first strand cDNA reagent mix (Superscript II buffer, DTT, and dNTPs) and enzyme mix (SuperScript, ThermoScriptase, and RNAout) with the Primer-template mixture and incubating at the appropriate time and temperature. A second strand cDNA is then formed by mixing the first strand cDNA reaction with second strand reagent mix, containing secondary cDNA mix (depc-$H_2O$, Tris-HCl (pH7.0), $MgCl_2$, $(NH_4)SO_4$, beta-$NAD^+$, and dNTPs) and cDNA enzyme mix (Vent DNA polymerase, Amplitaq DNA polymerase, *E. coli* ligase, *E. coli* RNase H, and *E. coli* DNA polymerase I), followed by incubation at the appropriate times and temperatures. The resultant DNA is then denatured and mixed with a Promoter which is an extension of Nx, see FIG. 2 for details) to create a Promoter-template mixture. The Promoter can also contain the full promoter with the tag/adapter or the remainder of the promoter sequence, depending on what was used as $N_x$ above. Formation of a DNA strand that can serve as a template for an IVT reaction is then accomplished by combining the Promoter—template mixture with Klenow fragment of *E. coli* DNA polymerase I and incubated at the appropriate times and temperatures (only the promoter region needs to be double stranded). Preferably, the Promoter is engineered to ensure that extension in the 3' direction is blocked. The resulting double-stranded (ds) cDNA contains a functional T7 RNA polymerase promoter, which is utilized for transcription. Finally, in vitro transcription (IVT) is performed by combining the (ds) cDNA with IVT reagent (buffer, NTP, DTT, RNase inhibitor, and T7 RNA polymerase), yielding amplified, antisense RNA.

The present invention can be combined with other processes to eliminate the need for multiple steps and varying reaction conditions and their associated problems. For example, see PCT/US00/20563, which is hereby incorporated by reference in its entirety. In preferred embodiments of the present invention, at least three otherwise separate enzymatic reactions can occur consecutively in one phase (i.e., without organic extraction and precipitation), more preferably in the same reaction vessel. Preferably, cDNA synthesis according to the present invention may occur in a modified low salt buffer. In addition, the invention may involve an enzyme mix, which may include a thermal stable DNA polymerase and reverse transcriptase for the production of cDNA, and RNA polymerase for RNA transcription. The enzyme activity may be inactivated at the appropriate step with either heat or chemical treatment (i.e., adjusting the salt concentration) or by the addition of an antibody specific to the enzyme.

Those skilled in the art will recognize that the products and methods embodied in the present invention may be applied to a variety of systems, including commercially available gene expression monitoring systems involving nucleic acid probe arrays, membrane blots, microwells, beads, and sample tubes, constructed with various materials using various methods known in the art. Accordingly, the present invention is not limited to any particular environment, and the following description of specific embodiments of the present invention is for illustrative purposes only.

In a preferred embodiment, the present invention can involve the amplification of nucleic acids, such as mRNA. However, other nucleic acids may be amplified such as by synthesizing double-stranded DNA from a single-stranded DNA population, and producing multiple copies of RNA from the double-stranded DNA, where the synthesizing and producing occur in reaction vessels, preferably in the same reaction vessel.

The reaction vessel according to the present invention may include a membrane, filter, microscope slide, microwell, sample tube, array, or the like. See International Patent applications No. PCT/US95/07377 and PCT/US96/11147, which are expressly incorporated herein by reference. The reaction vessel may be made of various materials, including polystyrene, polycarbonate, plastics, glass, ceramic, stainless steel, or the like. The reaction vessel may preferably have a rigid or semi-rigid surface, and may preferably be conical (e.g., sample tube) or substantially planar (e.g., flat surface) with appropriate wells, raised regions, etched trenches, or the like. The reaction vessel may also include a gel or matrix in which nucleic acids may be embedded. See A. Mirzabekov et al., *Anal. Biochem.* 259 (1):34–41 (1998), which is expressly incorporated herein by reference.

The single-stranded or double-stranded DNA populations according to the present invention may refer to any mixture of two or more distinct species of single-stranded mRNA, DNA or double-stranded DNA, which may include DNA representing genomic DNA, genes, gene fragments, oligonucleotides, polynucleotides, nucleic acids, PCR products, expressed sequence tags (ESTs), or nucleotide sequences corresponding to known or suspected single nucleotide polymorphisms (SNPs), having nucleotide sequences that may overlap in part or not at all when compared to one another. The species may be distinct based on any chemical or biological differences, including differences in base composition, order, length, or conformation. The single-stranded DNA population may be isolated or produced according to methods known in the art, and may include single-stranded cDNA produced from a mRNA template, single-stranded DNA isolated from double-stranded DNA, or single-stranded DNA synthesized as an oligonucleotide. The double-stranded DNA population may also be isolated according to methods known in the art, such as PCR, reverse transcription, and the like.

Where the nucleic acid sample contains RNA, the RNA may be total RNA, poly(A)+ RNA, mRNA, rRNA, or tRNA, and may be isolated according to methods known in the art. See, e.g, T. Maniatis et al., *Molecular Cloning: A Laboratory Manual*, 188–209 (Cold Spring Harbor Lab., Cold Spring Harbor, N.Y. 1982, which is expressly incorporated herein by reference. The RNA may be heterogeneous, referring to any mixture of two or more distinct species of RNA. The species may be distinct based on any chemical or biological differences, including differences in base composition, length, or conformation. The RNA may contain full length mRNAs or mRNA fragments (i.e., less than full length) resulting from in vivo, in situ, or in vitro transcriptional events involving corresponding genes, gene fragments, or other DNA templates. In a preferred embodiment, the mRNA population of the present invention may contain single-stranded poly(A)+ RNA, which may be obtained from a RNA mixture (e.g., a whole cell RNA preparation), for example, by affinity chromatography purification through an oligo-dT cellulose column.

Methods of isolating total mRNA are well known to those of skill in the art. For example, methods of isolation and purification of nucleic acids are described in detail in Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993) and Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993)).

In a preferred embodiment, the total RNA is isolated from a given sample using, for example, an acid guanidinium-phenol-chloroform extraction method and polyA+ mRNA is isolated by oligo dT column chromatography or by using (dT)n magnetic beads. (See e.g., Sambrook et al., Molecular Cloning: A Laboratory Manual (2nd ed.), Vols. 1–3, Cold Spring Harbor Laboratory, (1989), or Current Protocols in Molecular Biology, F. Ausubel et al., ed. Greene Publishing and Wiley-Interscience, New York (1987), which are incorporated by reference in their entireties for all purposes). (See also PCT/US99/25200 for complexity management and other sample preparation techniques, which is hereby incorporated by reference in its entirety for all purposes.) Where the single-stranded DNA population of the present invention is cDNA produced from a mRNA population, it may be produced according to methods known in the art. (See, e.g, Maniatis et al., supra, at 213–46.) In a preferred embodiment, a sample population of single-stranded poly(A)+ RNA may be used to produce corresponding cDNA in the presence of reverse transcriptase, oligo-dT primer(s) and dNTPs. Reverse transcriptase may be any enzyme that is capable of synthesizing a corresponding cDNA from an RNA template in the presence of the appropriate primers and nucleoside triphosphates. In a preferred embodiment, the reverse transcriptase may be from avian myeloblastosis virus (AMV), Moloney murine leukemia virus (MMuLV) or Rous Sarcoma Virus (RSV), for example, and may be thermal stable (e.g., rTth DNA polymerase available from PE Applied Biosystems, Foster City, Calif.).

In a preferred embodiment of the present invention, the single-stranded cDNA produced using a mRNA population as template may be separated from any resulting RNA templates by heat or enzyme treatment (e.g., RNase H). In a preferred embodiment, terminal transferase may be used to add poly(A) or poly(G) sequences to the 3'-termini of the single-stranded DNA. The double-stranded DNA of the present invention may be synthesized from the heterogeneous single-stranded DNA.

An oligonucleotide Primer may be applied to the poly(A), poly(G), poly(C) or poly(T) tailed heterogeneous single-stranded DNA. The oligonucleotide primer preferably includes a poly(T) or poly(C) region complementary to the poly(A) or poly(G) tail attached to the single-stranded DNA. In a preferred embodiment, amplification is accomplished through the use of two sequences; a Primer and a Promoter, the first used for cDNA synthesis and the second used for formation of a DNA strand that can serve as a template for an IVT reaction. In a further preferred embodiment, the Promoter includes a full or partial promoter consensus sequence capable of facilitating transcription by the RNA polymerase used, for example, the DNA-directed RNA polymerases derived from bacteriophage T7, T3 or SP6.

Any of the preferred oligonucleotide Primer or Promoter may be synthesized, for example, using a PCR-MATE Model 391 DNA synthesizer (Applied Biosystems) and purified by high-performance liquid chromatography before use. Oligonucleotides of sufficient length, quality sequence and base composition are also available from a large number of commercial vendors, including Genset, Operon, MWG, Research Genetics, and Life Technologies Inc. (LTI). Reverse transcriptase (e.g., either derived from AMV or MuLV) is available from a large number of commercial sources including Invitrogen/LTI, Amersham Phamacia Biotech (APB)/USB, Qiagen, and others. Other enzymes required or desired are also available from these vendors among others, such as Promega, and Epicentre. Nucleotides such as dNTPS, unique nucleotide sequences, and β-NAD are available from a variety of commercial sources such as APB, Roche Biochemicals, Sigma Chemicals. Buffers, salts and cofactors required or desired for these reactions can usually be purchased from the vendor that supplies a respective enzyme or assembled from materials commonly available, e.g., from Sigma Chemical.

Second strand DNA synthesis may occur to yield the double-stranded DNA. see e.g., Examples, infra.

In a preferred embodiment of the present invention, the ends of the double-stranded DNA may be blunted to prevent any concatenation of the double-stranded DNA. T4 DNA polymerase or *Escherichia coli* DNA polymerase I (Klenow fragment), for example, may be used preferably to produce blunt ends in the presence of the appropriate dNTPs. Also, the Promoter is preferably blocked from extension using methods that are conventional in the art. For example, they can be blocked at the 3' end by a phosphate or an amino group or a dideoxy base. Preferably, they can be blocked using a phosphate group. Blocked oligonucleotides can be purchased directly from commercial vendors such as those listed above.

Multiple copies of RNA according to the present invention may be obtained by in vitro transcription from the DNA preferably using T7 RNA polymerase in the presence of the appropriate nucleoside triphosphates.

In a preferred embodiment of the present invention, the multiple copies of RNA may be labeled by the incorporation of biotinylated, fluorescently labeled or radiolabeled CTP or UTP during the RNA synthesis. See U.S. Pat. Nos. 5,800,992, 6,040,138 and International Patent Application PCT/US96/14839, which is expressly incorporated herein by reference. Alternatively, labeling of the multiple copies of RNA may occur following the RNA synthesis via the attachment of a detectable label in the presence of terminal transferase. In a preferred embodiment of the present invention, the detectable label may be radioactive, fluorometric, enzymatic, or colorimetric, or a substrate for detection (e.g., biotin). Other detection methods, involving characteristics such as scattering, IR, polarization, mass, and charge changes, may also be within the scope of the present invention.

In a preferred embodiment, the amplified DNA or RNA of the present invention may be analyzed with a gene expression monitoring system. Several such systems are known. See, e.g., U.S. Pat. No. 5,677,195; Wodicka et al., *Nature Biotechnology* 15:1359–1367 (1997); Lockhart et al., *Nature Biotechnology* 14:1675–1680 (1996), which are expressly incorporated herein by reference. A preferred gene expression monitoring system according to the present invention may be a nucleic acid probe array, such as the GeneChip® nucleic acid probe array (Affymetrix, Santa Clara, Calif.). See U.S. Pat. Nos. 5,744,305, 5,445,934, 5,800,992, 6,040,193 and International Patent applications PCT/US95/07377, PCT/US96/14839, and PCT/US96/14839, which are expressly incorporated herein by reference. A nucleic acid probe array preferably comprises nucleic acids bound to a substrate in known locations. In other embodiments, the system may include a solid support or substrate, such as a membrane, filter, microscope slide, microwell, sample tube, bead, bead array, or the like. The solid support may be made of various materials, including paper, cellulose, gel, nylon, polystyrene, polycarbonate, plastics, glass, ceramic, stainless steel, or the like including any other support cited in U.S. Pat. No. 5,744,305 or U.S. Pat. No. 6,040,193. The solid support may preferably have a rigid or semi-rigid surface, and may preferably be spherical (e.g., bead) or substantially planar (e.g., flat surface) with appropriate wells, raised regions, etched trenches, or the like. The solid support may also include a gel or matrix in which nucleic acids may be embedded. The gene expression monitoring system, in a preferred embodiment, may comprise a nucleic acid probe array (including an oligonucleotide array, a cDNA array, a spotted array, and the like), membrane blot (such as used in hybridization analysis such as Northern, Southern, dot, and the like), or microwells, sample tubes, beads or fibers (or any solid support comprising bound nucleic acids). See U.S. Pat. Nos. 5,770,722, 5,744,305, 5,677,195 5,445,934, and 6,040,193 which are incorporated here in their entirety by reference. See also Examples, infra. The gene expression monitoring system may also comprise nucleic acid probes in solution.

The gene expression monitoring system according to the present invention may be used to facilitate a comparative analysis of expression in different cells or tissues, different subpopulations of the same cells or tissues, different physiological states of the same cells or tissue, different developmental stages of the same cells or tissue, or different cell populations of the same tissue. See U.S. Pat. Nos. 5,800,922 and 6,040,138. In a preferred embodiment, the proportional amplification methods of the present invention can provide reproducible results (i.e., within statistically significant margins of error or degrees of confidence) sufficient to facilitate the measurement of quantitative as well as qualitative differences in the tested samples. The proportional amplification methods of the present invention may also facilitate the identification of single nucleotide polymorphisms (SNPs) (i.e., point mutations that can serve, for example, as markers in the study of genetically inherited diseases) and other genotyping methods from limited sources. See, e.g., Collins et al., 282 *Science* 682 (1998), which is expressly incorporated herein by reference. The mapping of SNPs can occur by any of various methods known in the art, one such method being described in U.S. Pat. No. 5,679,524, which is hereby incorporated by reference.

The RNA, single-stranded DNA, or double-stranded DNA population of the present invention may be obtained or derived from any tissue or cell source. Indeed, the nucleic acid sought to be amplified may be obtained from any biological or environmental source, including plant, virion, bacteria, fungi, or algae, from any sample, including body fluid or soil. In one embodiment, eukaryotic tissue is preferred, and in another, mammalian tissue is preferred, and in yet another, human tissue is preferred. The tissue or cell source may include a tissue biopsy sample, a cell sorted population, cell culture, or a single cell. In a preferred embodiment, the tissue source may include brain, liver, heart, kidney, lung, spleen, retina, bone, lymph node, endocrine gland, reproductive organ, blood, nerve, vascular tissue, and olfactory epithelium. In yet another preferred embodiment, the tissue or cell source may be embryonic or tumorigenic.

Tumorigenic tissue according to the present invention may include tissue associated with malignant and pre-neoplastic conditions, not limited to the following: acute lymphocytic leukemia, acute myelocytic leukemia, myeloblastic leukemia, promyelocytic leukemia, myelomonocytic leukemia, monocytic leukemia, erythroleukemia, chronic myelocytic (granulocytic) leukemia, chronic lymphocytic leukemia, polycythemia vera, lymphoma, Hodgkin's disease, non-Hodgkin's disease, multiple myeloma, Waldenstrom's macroglobulinemia, heavy chain disease, solid tumors, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. See Fishman et al., *Medicine,* 2d Ed. (J. B. Lippincott Co., Philadelphia, Pa. 1985), which is expressly incorporated herein by reference.

In yet another preferred embodiment of the present invention, a nucleic acid detection system, the proportionally amplified DNA or RNA, or fragments thereof, may be immobilized directly or indirectly to a solid support or substrate by methods known in the art (e.g., by chemical or photoreactive interaction, or a combination thereof). See U.S. Pat. Nos. 5,800,992, 6,040,138 and 6,040,193. The resulting immobilized nucleic acid may be used as probes to detect nucleic acids in a sample population that can hybridize under desired stringency conditions. Such nucleic acids may include DNA contained in the clones and vectors of cDNA libraries.

The materials for use in the present invention are ideally suited for the preparation of a kit suitable for the single-phase proportional amplification of nucleic acids. Such a kit may comprise reaction vessels, each with one or more of the various reagents, preferably in concentrated form, utilized in the methods. The reagents may comprise, but are not limited to the following: low modified salt buffer, appropriate nucleotide triphosphates (e.g. dATP, dCTP, dGTP, dTTP; or rATP, rCTP, rGTP, and UTP) reverse transcriptase, RNase H, thermal stable DNA polymerase, RNA polymerase, and the appropriate primer complexes. In addition, the reaction vessels in the kit may comprise 0.2–1.0 ml tubes capable of fitting a standard thermocycler, which may be available singly, in strips of 8, 12, 24, 48, or 96 well plates depending on the quantity of reactions desired. Hence, the single-phase amplification of nucleic acids may be automated, e.g., performed in a PCR theromcycler. The thermocyclers may include, but are not limited to the following: Perkin Elmer 9600, MJ Research PTC 200, Techne Gene E, Erichrom, and Whatman Biometra T1 Thermocycler.

Also, the automated machine of the present invention may include an integrated reaction device and a robotic delivery system. In such cases, part of all of the operation steps may automatically be done in an automated cartridge. See U.S. Pat. Nos. 5,856,174, 5,922,591, and 6,043,080.

Without further elaboration, one skilled in the art with the preceding description can utilize the present invention to its fullest extent. The following examples are illustrative only, and not intended to limit the remainder of the disclosure in any way.

EXAMPLE ONE cDNA Synthesis

Step 1

Primer-template annealing. The HPLC purified Primer may be obtained from a −20° C. storage stock, prepared in a 100 $\mu$M solution with TE (10 mM Tris-HCl (pH 8.0) and 1 mM EDTA (pH 8.0) and diluted 1:1 with glycerol (for a final concentration of 50 $\mu$M in 50% glycerol and 50% TE). Where the desired nucleic acid sample is poly(A)+ RNA, a $T_{20}$ primer which is attached to a unique nucleic acid sequence that is a part of a RNA promoter, for example. In such case, an RNA sample (10 to 100 ng mRNA or 1–2 ug total RNA suspended in 5.5 $\mu$l or less) can be mixed with 0.5 $\mu$l primer to give a final volume of 6 $\mu$l. The mixture can be incubated at 70° C. for 3 minutes, then cooled to 4° C.

Step 2

First strand cDNA synthesis. To the 6 $\mu$l Primer-template mixture, may be added 3 $\mu$l of RT buffer and 1 $\mu$l of RT enzyme mixture. This 10 $\mu$l reaction mixture may then be incubated at 37° C. for 20 minutes, 65° C. for 20 minutes, then cooled to 4° C. or on ice.

The RT buffer may be prepared in 150 $\mu$l aliquots for 50 reactions by combining 100 $\mu$l 5×1° cDNA buffer (shipped with Superscript II) 25 $\mu$l DTT (0.1 M), and 25 $\mu$l dNTP (10 mM).

The RT enzyme mixture may be prepared by combining SuperScript (200 U/$\mu$l), ThermoScriptase (15 U/$\mu$l), and RNAout (40 U/$\mu$l), all of which are available from Life Technologies, Inc., Gaithersburg, Md., in a 1:1:1 mixture.

Step 3

Second strand cDNA synthesis. The 10 $\mu$l first strand cDNA reaction mixture may be mixed with 9 $\mu$l secondary cDNA buffer and 1 $\mu$l secondary enzyme mix. This 20 $\mu$l reaction mixture may then be incubated at 16° C. for 105 minutes, 75° C. for 15 minutes, then cooled to 4° C. or on ice.

The secondary cDNA mix may be prepared in 450 $\mu$l aliquots for 50 reactions by combining 245 $\mu$l RNase-free H$_2$O, 40 $\mu$l of 1 M Tris HCl (pH 7.0), 35 $\mu$l of 0.1 M MgCl$_2$, 100 $\mu$l of 0.1 M (NH$_4$)$_2$SO$_4$, 15 $\mu$l of 10 mM beta-NAD$^+$, and 15 $\mu$l of 10 mM dNTP.

The cDNA enzyme mix may be prepared in 50 $\mu$l aliquots for 50 reactions by combining, in a screw-capped tube cooled to −20° C., 2 $\mu$l of Vent DNA polymerase (2 U/$\mu$l) (NEB, Inc., Beverly, Mass.), 5 $\mu$l of AmpliTaq DNA polymerase (5 U/$\mu$l) (PE Biosystems, Foster City, Calif.), 5 $\mu$l of E. coli ligase (10 U/$\mu$l) (available from, for example, NEB, Inc., Beverly, Mass.), 6 $\mu$l of E. coli RNase H (2 U/$\mu$l) (available from, for example, Promega, Inc., Madison, Wis.), and 25 $\mu$l of E. coli DNA polymerase I (10 U/$\mu$l) (available from, for example, NEB, Inc., Beverly, Mass.). This mixture may be total volume adjusted to 50 $\mu$l with 7 $\mu$l of 50% cold glycerol, followed by a brief and gentle mix and quick spin before storage at −20° C.

Step 4

Formation of a DNA strand for an IVT reaction . The 20 $\mu$l second strand cDNA reaction may be mixed with 1 $\mu$l of a Promoter that comprises the remainder of the promoter used in the first primer, also having an overlap with the primer used above so that it can hybridize. This mixture is heated to 95° C. for 5 minutes then cooled to 4° C. or on ice. The 21 $\mu$l reaction mixture may then be mixed with 0.5 $\mu$l (2.5 units) Klenow fragment of DNA polymerase I (available from, for example, NEB, Inc., Beverly, Mass.), incubated at 37° C. for 30 minutes, 72° C. for 15 minutes, then cooled to 4° C. or on ice.

Step 5

De-salting(optional step) Each reaction may be passed through a S-300 column (available from Amersham Pharmacia Biotech) spun at 1000×g for 1 minute.

cRNA Synthesis

Step 6

In vitro transcription. To achieve maximal amplification, the 22 $\mu$l total volume of double-stranded cDNA may be combined with 18 $\mu$l of IVT reagent, which may contain 4 $\mu$l of Enzo Buffer, 4 $\mu$l of NTP mix, 4 $\mu$l DTT, 4 $\mu$l RNase Inhibitor and 2 $\mu$l enzyme (all reagents from Enzo BioArray High yield RNA Transcript Labelling kit available from distributed by Affymetrix for Enzo Diagnostic Inc. Farmingdale, N.Y.).

The 40 $\mu$l total volume mixture may be incubated at 37° C. for 4–6 hours, but can be 30 minutes to many hours. The resulting samples may be stored at −20° C., or analyzed.

Analysis may occur through the resolution of a 0.5 $\mu$l or 1 $\mu$l sample on a 1% agarose gel. Purification or quantification of the nucleic acid sample may occur by any one of the methods known in the art.

EXAMPLE TWO

Analysis Using GeneChip® Probe Arrays

GeneChip® nucleic acid probe arrays are manufactured using technology that combines photolithographic methods and combinatorial chemistry. See the patents incorporated above. In a preferred embodiment, over 280,000 different oligonucleotide probes are synthesized in a 1.28 cm×1.28 cm area on each array. Each probe type is located in a specific area on the probe array called a probe cell. Measuring approximately 24 $\mu$m×24 $\mu$m, each probe cell contains more than $10^7$ copies of a given oligonucleotide probe.

Probe arrays are manufactured in a series of cycles. A glass substrate is coated with linkers containing photolabile protecting groups. Then, a mask is applied that exposes selected portions of the probe array to ultraviolet light.

Illumination removes the photolabile protecting groups enabling selective nucleotide phosphoramidite addition only at the previously exposed sites. Next, a different mask is applied and the cycle of illumination and chemical coupling is performed again. By repeating this cycle, a specific set of oligonucleotide probes is synthesized, with each probe type in a known physical location. The completed probe arrays are packaged into cartridges. These arrays are commercially available through Affymetrix Inc., Santa Clara, Calif.

The amplified RNA molecules are made as shown in Example 1 above. Labeled nucleotides are incorporated into the RNA during the IVT reaction. Then the RNA is fragmented and incubated with the array. The preferred label is biotin.

The hybridized probe array is stained with streptavidin phycoerythrin conjugate and scanned by the Hewlett-Packard (HP) GeneArray™ Scanner See U.S. Pat. Nos. 5,744,305 and 5,445,934. The areas of hybridization are inputted into a computer and translated into information as to which nucleic acid sequences were present in the original sample. See PCT/US00/20563.

EXAMPLE 3

An example of an amplification using total RNA was run in a process similar of that of Example 1. The 1st strand primer was 5' GAGGCGGATTCACCGT-CATTTTTTTTTTTTTTTTTTTTTTTT3' and the 3rd strand Promoter (which also acted as a primer here) was 5'GGCCAGTGAATTGTAATACGACTCAC-TATAGGGAGGCGGATTCACCGTC A3'.

The specific embodiments described above do not limit the scope of the present invention in any way as they are single illustrations of individual aspects of the invention. Functionally equivalent methods and components are within the scope of the invention. The scope of the appended claims thus includes modifications that will become apparent to those skilled in the art from the foregoing description.

We claim:

1. A method for the amplification of nucleic acid, said method comprising:

contacting mRNA having a poly d(A) tail with a primer consisting of SEQ ID No. 2;

generating a first cDNA strand from the mRNA strand by extending the primer by reverse transcriptase and the appropriate nucleotides under the appropriate conditions, which creates a RNA:DNA duplex;

denaturing the RNA:DNA duplex;

forming a double stranded DNA;

adding a promoter to the DNA by hybridizing an oligonucleotide consisting of SEQ ID No. 4 to the single stranded DNA, wherein the oligonucleotide is blocked from extension at the 3' end;

forming a double stranded DNA promoter region by adding the appropriate reagents; and, producing multiple copies of RNA from the DNA strand comprising the promoter.

2. The method of claim 1, wherein any enzymes used are thermostable.

3. The method of claim 1 wherein said nucleic acid is selected from the group consisting of genomic DNA, cDNA, total RNA, poly(A)+ RNA, and oligonucleotides.

4. The method of claim 1 wherein said poly(A)+ RNA is mRNA.

5. The method of claim 1 further comprising:

contacting said multiple copies of RNA with a solid support comprising nucleic acid probes.

6. The method of claim 1 further comprising:

detecting the presence or absence of hybridization of said multiple copies of RNA to said nucleic acid probes on said solid support.

7. The method of claim 1 wherein said solid support comprising nucleic acid probes is selected from the group consisting of a nucleic acid probe array, a membrane blot, a microwell, a bead, and a sample tube.

8. The method of claim 1 wherein said nucleic acid is isolated from an eukaryotic cell or tissue.

9. The method of claim 8, wherein said eukaryotic cell or tissue is mammalian.

10. The method of claim 9 wherein said mammalian cell or tissue is human.

11. The method of claim 1 wherein said nucleic acid is isolated from a source selected from the group consisting of dissected tissue, microdissected tissue, a tissue subregion, a tissue biopsy sample, a cell sorted population, a cell culture, and a single cell.

12. The method of claim 1 wherein said nucleic acid is isolated from a cell or tissue source selected from the group consisting of brain, liver, heart, kidney, lung, spleen, retina, bone, lymph node, endocrine gland, reproductive organ, blood, nerve, vascular tissue, and olfactory epithelium.

13. The method of claim 1 wherein said nucleic acid is isolated from a cell or tissue source selected from the group consisting of embryonic and tumorigenic.

14. The method of claim 1 wherein the method involves the use of an automated machine.

15. The method of claim 14 wherein said automated machine is selected from the group consisting of a thermocycler, an integrated reaction device, and a robotic delivery system.

* * * * *